United States Patent
Sasaki et al.

(10) Patent No.: US 9,733,327 B2
(45) Date of Patent: *Aug. 15, 2017

(54) NMR IMAGING DEVICE WITH PROBE, MAGNETIC FIELD GENERATOR AND IMAGE PROCESSOR USING TRANSVERSE RELAXATION TIME ($T_2^L$) AND NMR IMAGING METHOD FOR PERFORMING $T_2^L$ IMAGING

(71) Applicant: JAPAN SCIENCE AND TECHNOLOGY AGENCY, Kawaguchi-shi, Saitama (JP)

(72) Inventors: Susumu Sasaki, Niigata (JP); Tatsuro Yuge, Toyonaka (JP); Yoshiro Hirayama, Sendai (JP)

(73) Assignee: JAPAN SCIENCE AND TECHNOLOGY AGENCY, Kawaguchi-shi, Saitama (JP)

( * ) Notice: Subject to any disclaimer, the term of this patent is extended or adjusted under 35 U.S.C. 154(b) by 362 days.

This patent is subject to a terminal disclaimer.

(21) Appl. No.: 14/367,411

(22) PCT Filed: Dec. 18, 2012

(86) PCT No.: PCT/JP2012/082739
§ 371 (c)(1),
(2) Date: Jun. 20, 2014

(87) PCT Pub. No.: WO2013/094582
PCT Pub. Date: Jun. 27, 2013

(65) Prior Publication Data
US 2014/0375317 A1    Dec. 25, 2014

(30) Foreign Application Priority Data
Dec. 21, 2011   (JP) .................... 2011-280016

(51) Int. Cl.
*G01R 33/50*   (2006.01)
*G01R 33/56*   (2006.01)
(Continued)

(52) U.S. Cl.
CPC .............. *G01R 33/50* (2013.01); *G01N 24/08* (2013.01); *G01R 33/34* (2013.01); *G01R 33/56* (2013.01); *H01L 22/12* (2013.01)

(58) Field of Classification Search
CPC ........ G01R 33/50; G01R 33/56; G01R 33/34; G01N 24/08; H01L 22/12
See application file for complete search history.

(56) References Cited

U.S. PATENT DOCUMENTS 5,245,286 A  *  9/1993  Carlson ............ G01R 33/56563
                                                     324/319
2005/0016221 A1    1/2005  Bruske et al.
(Continued)

FOREIGN PATENT DOCUMENTS

CN    1576875 A    2/2005
CN    101002677 A    7/2007
(Continued)

OTHER PUBLICATIONS

Katsumi Kose, Compact MRI, Nov. 15, 2004, pp. 64-79, 1st edition, 1st print.
(Continued)

*Primary Examiner* — G. M. Hyder
(74) *Attorney, Agent, or Firm* — Sughrue Mion PLLC (57) ABSTRACT

In order to provide an NMR imaging device capable of distinguishing substances that cannot be distinguished by $T_2^H$, an NMR imaging device (1) according to this invention includes: a probe (3) capable of housing a sample in a static gradient magnetic field; an application portion (5) configured to apply a π pulse having a Larmor frequency corre-
(Continued)

sponding to the static gradient magnetic field at a predetermined position of the sample to the sample in a multiplexed manner at a predetermined time interval; and an image processing portion (7) configured to determine a relaxation time based on a nuclear magnetic resonance signal of the sample, and perform imaging of the relaxation time.

14 Claims, 8 Drawing Sheets

(51) Int. Cl.
G01R 33/34 (2006.01)
G01N 24/08 (2006.01)
H01L 21/66 (2006.01)

(56) References Cited

U.S. PATENT DOCUMENTS

2005/0017719 A1   1/2005   Heubes
2007/0145976 A1   6/2007   Asano

FOREIGN PATENT DOCUMENTS

CN   101545877 A    9/2009
JP   63-311943 A   12/1988
JP   10-277006 A   10/1998
KR   20050078996 A   8/2005

OTHER PUBLICATIONS

Tatsuro Yuge et al., "Determination of fluctuation spectrum by multiple pulse sequence", Abstracts of the Meeting of the Physical Society of Japan, Mar. 3, 2011, pp. 181, (25pRB-8).
Susumu Sasaki et al., "Direct observation of low-frequency spectra of noise in solids that breaks the nuclear-spin coherence", Abstracts of the Meeting of the Physical Society of Japan, Mar. 3, 2011, pp. 181,(25pRB-7).
Susumu Sasaki et al., "Enhancement of nuclear-spin coherence and noise spectra in solids caused by multiple inversion pulse irradiation". Abstracts of the Meeting of the Physical Society of Japan, Aug. 24, 2011, pp. 123, (21aED-4).
Tatsuro Yuge et al., "Measurement of the Noise Spectrum Using a Multiple-Pulse Sequence", Physical Review Letters, Oct. 21, 2011, pp. 170504-1-170504-4, vol. 107, No. 17.
Communication dated Oct. 9, 2015 from the State Intellectual Property Office of the People's Republic of China in counterpart application No. 201280060866.0.
Zhang Pei Hua, "Clinical Vascular Surgery", Jan. 31, 2007. Science Press, China, p. 113.
Zhang Ze Bao, "Basic Medical Imaging Physics", Sep. 30, 1994, Liaoning Science & Technology Publishing House, China, p. 190.
Musse M et al: "An investigation of the structural aspects of the tomato fruit by means of quantitative nuclear magnetic resonance imaging", Magnetic Resonance Imaging, Elsevier Science,vol. 27, No. 5, (2009), pp. 709-719, XP026132156, ISSN: 0730-725X, DOI:10.1016/J.MRI.2008.11.005.
Jenista E R et al: "Optimized, unequal pulse spacing in multiple echo sequences improves refocusing in magnetic resonance", The Journal of Chemical Physics, vol. 131, 204510, No. 20, Nov. 30, 2009 (Nov. 30, 2009), pp. 204510-1-204510-7, XP009184546, ISSN: 0021-9606, DOI: 10.1063/1.3263196.
Grucker D et al: "Chemical and molecular exchange effects on $T_2$ relaxation of living tissues: A pulse spacing dependence study", Biochimica Et Biophysica Acta, Elsevier, vol. 887, No. 3,1 (1986), pp. 249-255, XP023474375, ISSN: 0167-4889, DOI: 10.1016/0167-4889(86)90152-7.
Santyr G E et al: "Variation in measured transverse relaxation in tissue resulting from spin locking with the CPMG sequence", Journal of Magnetic Resonance, vol. 79, No. 1, (1988), pp. 28-44, XP023962061, ISSN: 0022-2364, DOI:10.1016/0022-2364(88)90320-4.
C F Maier et al: "T2 Quantitation of Articular Cartilage at 1.5T",Proc. Intl. Soc. Mag. Reson. Med. 10, (2002), p. 1846, XP055192527.
N. Hernandez-Sanchez et al: "An NMR study on internal browning in pears", Postharvest Biology and Technology, Elsevier, vol. 44, No. 3, Jan. 3, 2007 (2007), pp. 260-270, XP022024306, ISSN: 0925-5214, DOI:10.1016/j,postharybio.2007.01.002.
Alexander G. Gardener et al: "Dependence of blood $R_2$ relaxivity on CPMG echo-spacing at 2.35 and 7 T", Magnetic Resonance in Medicine, vol. 64, No. 4, Aug. 16, 2010 (Aug. 16, 2010), pp. 967-974, XP055192529, ISSN; 0740-3194, DOI: 10.1002/mrm.22575.
Nicholas J Schneiders et al: "Accurate $T_2$ NMR images", Med. Phys., vol. 10, No. 5, Sep. 1983 (1983), pp. 642-645, XP55060014.
Jens H Jensen et al: "Model for Interecho Time Dependence of the CPMG Relaxation Rate in Iron-Rich Brain Tissue",Proc. Intl. Soc. Mag. Reson. Med. 9, vol. 9, 21 (2001), p. 1365, XP055192530.
Michael J. Biercuk et al: "Phenomenological study of decoherence in solid-state spin qubits due to nuclear spin diffusion", Physical Review B, vol. 83, 235316, No. 23, Jun. 10, 2011 (2011), pp. 235316-1-235316-10 XP055192599, ISSN: 1098-0121, DOI: 10.1103/PhysRevB.83.235316.
Gonzalo A. Alvarez et al: "Measuring the Spectrum of Colored Noise by Dynamical Decoupling", Physical Review Letters, vol. 107, No. 23, 230501, Nov. 30, 2011 (2011), pp. 230501-1 230501-5, XP055192532, ISSN: 0031-9007, DOI: 10.1103/PhysRevLett.107.230501.
Jonas Bylander et al: "Noise spectroscopy through dynamical decoupling with a superconducting flux qubit",Nature Physics, vol. 7, No. 7, May 8, 2011 (May 8, 2011), pp. 565-570, XP055192534, ISSN: 1745-2473, DOI: 10.1038/NPHYS1994.
T. D. Ladd et al: "Coherence time of decoupled nuclear spins in silicon", Physical Review B, vol, 71, No. 1, 71, 014401, Jan. 2005 (2005), pp. 014401-1-014401-12 XP055192535, ISSN: 1098-0121, DOI:10.1103/PhysRevB.71.014401.
Herberg et al: "Characterization of local deformation in filled-silicone elastomers subject to high strain—NMR Mouse and Magnetic Resonance Imaging as a diagnostic tool for detection of inhomogeneities", Polymer Degradation and Stability , vol. 91, No. 8, (2006), pp. 1701-1710, XP005435750, ISSN: 0141-3910, DOI:19.1016/j.polymdegradstab.2005.12.006.
Communication dated Jun. 9, 2015 from the European Patent Office in counterpart European Application No. 12860186.1.

\* cited by examiner

A: GaAs (Si − doped)
B: GaAs (undoped)
C: GaAs (Cr − doped)

FIG. 7

$T_2^L$ IMAGE

FIG. 8

$T_2^H$ IMAGE

NMR IMAGING DEVICE WITH PROBE, MAGNETIC FIELD GENERATOR AND IMAGE PROCESSOR USING TRANSVERSE RELAXATION TIME ($T_2^L$) AND NMR IMAGING METHOD FOR PERFORMING $T_2^L$ IMAGING

CROSS REFERENCE TO RELATED APPLICATIONS

This application is a National Stage of International Application No. PCT/JP2012/082739 filed Dec. 18, 2012, claiming priority based on Japanese Patent Application No. 2011-280016 filed Dec. 21, 2011, the contents of all of which are incorporated herein by reference in their entirety.

TECHNICAL FIELD

This invention relates to an NMR imaging device and an NMR imaging method.

BACKGROUND ART

Nuclear magnetic resonance (NMR) is a phenomenon that a resonance occurs between a magnetic field and an atomic nucleus when a nuclear spin that is precessing in the magnetic field is applied with a rotating magnetic field having the same frequency as a Larmor frequency of the precession.

Because relaxation characteristics for the nuclear spin to return to an original state after changing the state due to the resonance are different depending on a situation of the nuclear spin, it is possible to identify a bonding structure or physical properties of an object to be measured.

More specifically, for example, an oscillating magnetic field resonating in a pulse-like manner is applied to a nuclear spin directed to be parallel or antiparallel to a magnetic field in a static magnetic field, the static magnetic field is applied in a center axis (Z axis) direction, so as to change the spin direction in an XY axis direction. After that, a period of time for the spin direction to return to the original direction (the period of time is referred to as "a relaxation time") is measured so as to identify the bonding structure or the physical properties of the object to be measured.

Further, the relaxation time includes a vertical relaxation time $T_1$ that is a relaxation time of a component in a center axis direction (Z axis direction) of the spin precession before the pulse is introduced, and a transverse relaxation time $T_2$ that is a relaxation time of a component in a direction (XY axis direction) perpendicular to the center axis direction.

A measurement result of this nuclear spin relaxation state is imaged to be a magnetic resonance image (MRI). The bonding structure or the physical properties of the object to be measured are imaged based on the vertical relaxation time $T_1$ and/or the transverse relaxation time $T_2$.

Here, when imaging is performed based on the transverse relaxation time $T_2$, a method of measuring $T_2$ by Hahn echo is usually adopted (Patent Document 1).

PRIOR ART DOCUMENT

Patent Document

Patent Document 1: JP-A-H10-277006

DISCLOSURE OF THE INVENTION

Problem to be Solved by the Invention

However, when imaging is performed by measuring $T_2$ ($T_2^H$) by Hahn echo, $T_2^H$ is affected by static noise received by the object to be measured. Therefore, there is a problem in that a difference between values of $T_2^H$ is too small to distinguish substances by MRI, fairly depending on a bonding state of the object to be measured, an external environment, or the like. It is noted here that the values are obtained by measuring different samples, with different dopants, at different measurement positions, or the like, and are compared to each other.

Specifically, for example, the difference of $T_2^H$ becomes smaller as a difference of an electron density of the object to be measured becomes smaller in a case where the object to be measured is a semiconductor substrate. Therefore, it may be difficult to distinguish by MRI a substance such as a semiconductor in which different impurities are doped.

This invention has been made in view of the above-mentioned problem, and an object thereof is to provide an NMR imaging device capable of distinguishing substances that cannot be distinguished by $T_2^H$.

Means to Solve the Problem

In order to achieve the above-mentioned object, the inventors of this invention found after keen examination that there is a predetermined relationship between a signal attenuation constant $T_2^L$ (generalized transverse relaxation time) of an NMR signal in a case where a π pulse is applied to the object to be measured at a predetermined interval (in a multiplexed manner) and dynamic noise received by the spin of the object to be measured from an external environment.

Further, the inventors found that it is possible to realize the MRI capable of clearly distinguishing the object to be measured that cannot be distinguished by $T_2^H$, in which the relaxation characteristics reflecting not the static noise due to the external environment but dynamic noise are extracted through imaging of $T_2^L$ by applying the π pulse signal to the sample at a predetermined time interval considering noise received by nuclear species of the object to be measured from the external environment. Thus, this invention has been made.

According to a first aspect of this invention, there is provided an NMR imaging device, which comprises:

a probe capable of housing a sample in a static gradient magnetic field;

an application portion configured to apply a π pulse to the sample in a multiplexed manner at a predetermined time interval, the π pulse having a Larmor frequency corresponding to the static gradient magnetic field at a predetermined position of the sample; and an image processing portion configured so as to determine a transverse relaxation time based on converged attenuation characteristics of a nuclear magnetic resonance (NMR) signal of the sample obtained when multiple pulses are applied, and perform imaging of the transverse relaxation time, the NMR signal and the transverse relaxation time having a relationship shown in the following expression (1), the predetermined time interval of the π pulse and a frequency of noise received by the sample from an external environment being expressed by the following expression (2). In the first aspect of this invention, the NMR imaging device is configured so as to:

determine a predetermined time interval 2τ of the π pulse based on a frequency f of noise received by a nuclear spin in the expression (2) by utilizing a fact that the transverse relaxation time determined from the expression (1) indicates an amplitude of the noise corresponding to the frequency having a relationship of the expression (2) with the predetermined time interval of the π pulse;

measure the NMR signal at the predetermined time interval 2τ of the π pulse; and determine an attenuation curve of intensity of the NMR signal based on a measurement result of the NMR signal, thereby determining the transverse relaxation time ($T_2^L$) based on the expression (1):

$$W(t) \sim \exp(-t/T_2^L) \tag{1}$$

W(t): NMR signal intensity
$T_2^L$: signal attenuation constant (transverse relaxation time)
t: time $$f = \frac{1}{4\tau} \tag{2}$$

f: frequency of noise received by nuclear spin
τ: (a half of) π pulse interval.

According to a second aspect of this invention, there is provided an NMR imaging method, which comprises the steps of:

(a) placing a sample in a static gradient magnetic field;

(b) applying a π pulse to the sample in a multiplexed manner at a predetermined time interval, the π pulse having a Larmor frequency corresponding to the static gradient magnetic field at a predetermined position of the sample; and (c) determining a transverse relaxation time based on converged attenuation characteristics of a nuclear magnetic resonance (NMR) signal of the sample obtained when multiple pulses are applied, and performing imaging of the transverse relaxation time, the nuclear magnetic resonance signal and the transverse relaxation time having a relationship shown in the following expression (1), the predetermined time interval of the π pulse and a noise being expressed by the following expression (2). In the second aspect of this invention, the step (c) comprises:

determining a predetermined time interval 2τ of the π pulse based on a frequency f of noise received by a nuclear spin in the expression (2) by utilizing a fact that the transverse relaxation time determined from the expression (1) indicates an amplitude of the noise corresponding to the frequency having a relationship of the expression (2) with the predetermined time interval of the π pulse;

measuring the NMR signal at the predetermined time interval 2τ of the π pulse; and determining an attenuation curve of intensity of the NMR signal based on a measurement result of the NMR signal, thereby determining the transverse relaxation time ($T_2^L$) based on the expression (1).

$$W(t) \sim \exp(-t/T_2^L) \tag{1}$$

W(t): NMR signal intensity
$T_2^L$: signal attenuation constant (transverse relaxation time)
t: time $$f = \frac{1}{4\tau} \tag{2}$$

f: frequency of noise received by nuclear spin
τ: (a half of) π pulse interval.

Effect of the Invention

According to this invention, it is possible to provide the NMR imaging device capable of distinguishing substances that cannot be distinguished by $T_2^H$.

MODE FOR EMBODYING THE INVENTION

Now, descriptions will be made as regards embodiments of this invention in detail with reference to the drawings.

First, a first embodiment of this invention is described.

To begin with, a principle of nuclear magnetic resonance imaging of this invention is described.

First, a magnetic pulse (here, π pulse) is applied to a sample as an object to be measured. The magnetic pulse having a Larmor frequency corresponding to a static magnetic field at a point to be measured.

Figure 1:
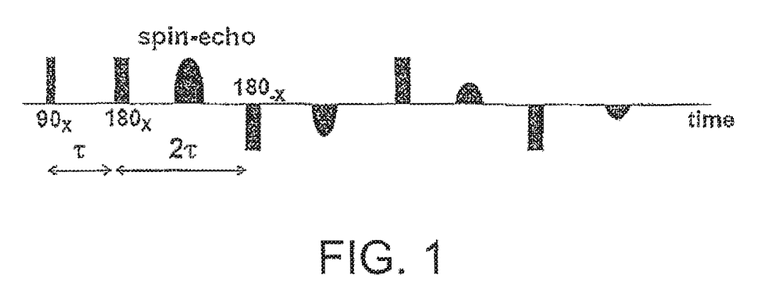
FIG. 1 is a view showing an example of a multiplexed π pulse for use in this invention.

Specifically, a multiplexed π pulse as shown in FIG. 1 is applied. A pulse applying interval is 2τ in this embodiment.

Further, τ means a half time of a π pulse interval, that is, the pulse applying interval (see FIG. 1).

In nuclear species of the object to be measured applied with the magnetic pulse, which resonate with the magnetic pulse, a spin direction of the precession changes due to the nuclear magnetic resonance, and then, uniform phases of spins become disturbed while outputting a nuclear magnetic resonance signal (NMR signal). After the π pulse is applied in a multiplexed manner for a sufficiently long period of time (in sufficient amount), the following relationship (1) is satisfied between intensity of the nuclear magnetic resonance signal and time.

$$W(t) \sim \exp(-t/T_2^L) \quad (1)$$

W(t): NMR signal intensity
$T_2^L$: signal attenuation constant (relaxation time)
t: time In this case, a signal attenuation constant (here, referred to as a generalized transverse relaxation time) $T_2^L$ depends on the π pulse interval 2τ, and further, the following relationship (2) is satisfied between the π pulse interval 2τ and a frequency f related to measurement among frequencies of noise received by a nuclear spin from an external environment (fluctuation of fluctuating magnetic field).

$$f = \frac{1}{4\tau} \quad (2)$$

f: frequency of noise received by nuclear spin
τ: (a half of) π pulse interval.

As understood from the relationships (1) and (2), noise contributing to the generalized transverse relaxation time $T_2^L$ is limited to one satisfying the relationship (2). Therefore, by changing the π pulse interval 2τ so as to obtain the NMR signal, it is possible to measure a spectrum of the noise.

In this invention, utilizing this fact, the π pulse having a predetermined pulse interval considering the noise received by the nuclear species of the object to be measured from the external environment is introduced to the sample, so as to obtain the generalized transverse relaxation time $T_2^L$ for performing imaging.

Figure 2:
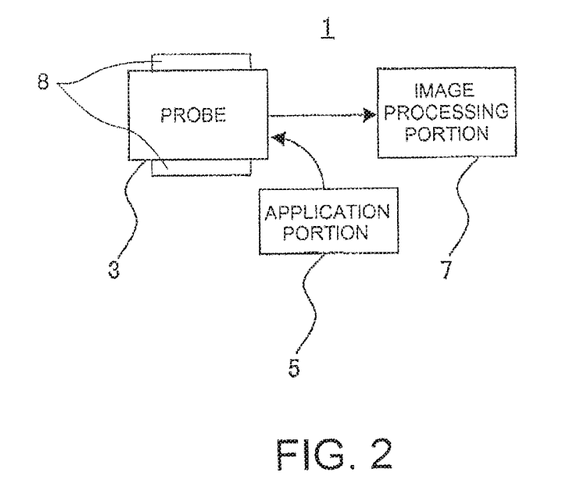
FIG. 2 is a schematic diagram illustrating a structure of an NMR imaging device 1 according to a first embodiment of this invention.

Next, with reference to FIG. 2, a structure of an NMR imaging device 1 according to a first embodiment is described.

As illustrated in FIG. 2, the NMR imaging device 1 includes a probe 3 configured to house the object to be measured, to which a static gradient magnetic field is applied (the sample can be housed in the static gradient magnetic field), an application portion 5 configured to apply the magnetic pulse to the probe 3, and an image processing portion 7 configured to perform imaging of the generalized transverse relaxation time $T_2^L$ based on the nuclear magnetic resonance signal output from the sample.

Here, in FIG. 2, an amplifier for amplifying the magnetic pulse, a cooling device for cooling the device, and the like are not illustrated except for a coil (magnetic field generating portion) 8 for applying the static magnetic field and the static gradient magnetic field.

Figure 3:
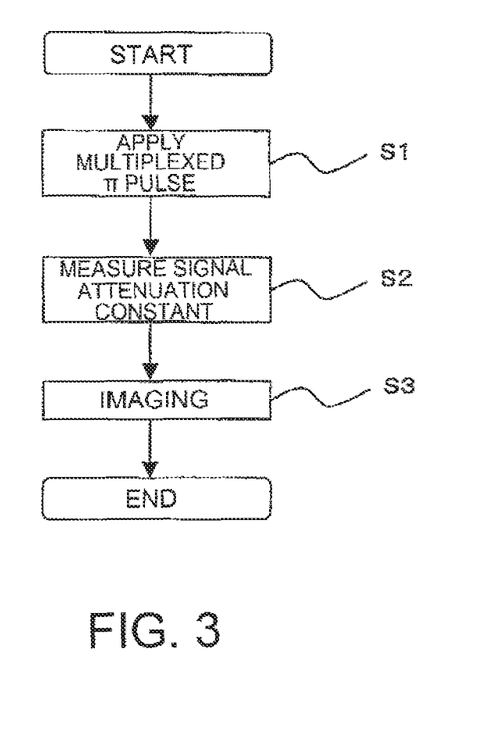
FIG. 3 is a flowchart illustrating an operation of the NMR imaging device 1.
Figure 4:
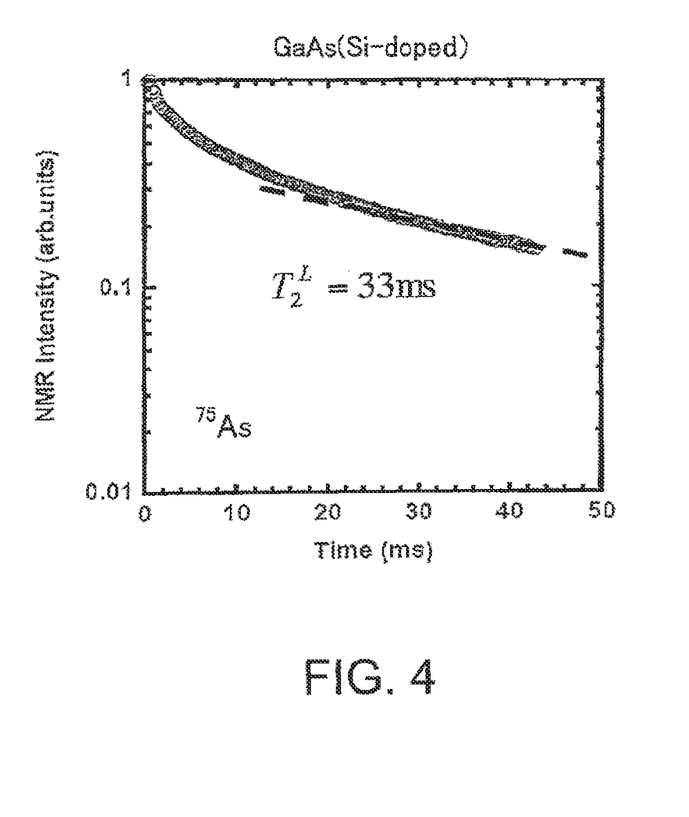
FIG. 4 is a graph showing a relationship between an NMR signal and time when the multiplexed π pulse shown in FIG. 1 is applied to Si-doped GaAs in an example of this invention.

Next, with reference to FIGS. 2 to 4, an imaging method using the NMR imaging device 1 according to the first embodiment is described.

First, the object to be measured is placed in the probe 3 illustrated in FIG. 2, and the static gradient magnetic field is applied by using the coil 8 and the like, while the magnetic pulse is introduced into the probe 3 by using the application portion 5 so that the sample is applied with the multiplexed π pulse (S1 in FIG. 3).

Further, the π pulse interval 2τ in this case is determined in accordance with the external environment of the sample considering the noise sensed by the nuclear species of the object to be measured (received from the external environment). Specifically, if the sample is a semiconductor as an example described later, for example, the π pulse interval 2τ corresponding to a frequency range in which an interaction between carriers and the nuclear spins causes noise is selected.

In addition, if the sample is a living body, the π pulse interval 2τ corresponding to a frequency range supporting a biological reaction and a response speed of a specific part of an organ is selected.

Next, the signal attenuation constant $T_2^L$ is determined from the NMR signal (S2 in FIG. 3).

Specifically, the sample applied with the multiplexed π pulse outputs the NMR signal. When a predetermined period of time elapses (in other words, a sufficient number of π pulses are introduced), a logarithm of intensity of the NMR signal is attenuated in proportion to time as shown in FIG. 4 (see expression (1)).

In this attenuation curve, a proportionality constant (the reciprocal thereof) that is the generalized transverse relaxation time $T_2^L$ is determined.

Finally, the image processing portion 7 performs imaging of $T_2^L$ by expressing a length of the generalized transverse relaxation time $T_2^L$ with density of color, for example (S3 in FIG. 3).

In this way, according to the first embodiment, the NMR imaging device 1 applies the π pulse to the sample at the predetermined time interval 2τ in a multiplexed manner so as to perform imaging of the generalized (transverse) relaxation time based on the nuclear magnetic resonance signal of the sample.

Therefore, it is possible to perform imaging while considering a dynamic noise f sensed by the nuclear species of the object to be measured (received from the external environment). Therefore, even if a static noise due to a bonding state of the object to be measured or the external environment is the same, it is possible to distinguish the object.

In addition, because the π pulse interval 2τ can be controlled in a wide range, the MRI imaging suitable for the object to be measured can be performed by selecting the π pulse interval 2τ corresponding to the object to be measured.

Next, a second embodiment of this invention is described with reference to FIG. 10.

The second embodiment is an example in which an image of generalized relaxation time is obtained by changing a measurement position and the π pulse interval 2τ with respect to the object to be measured in the first embodiment.

Further, the NMR imaging device 1 used in the second embodiment is the same as that used in the first embodiment, and therefore a description thereof is omitted.

Figure 10:
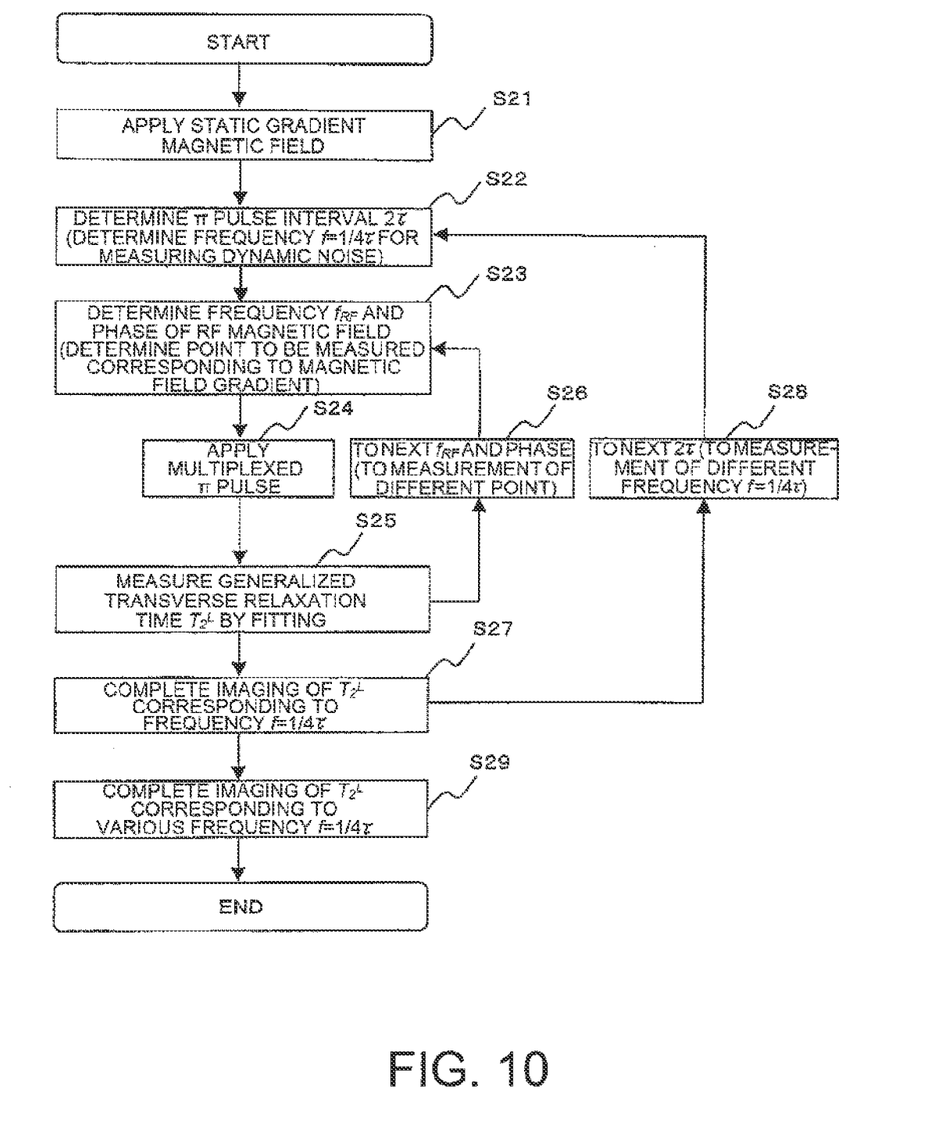
FIG. 10 is a flowchart illustrating a procedure of a second embodiment of this invention.

First, the object to be measured is placed in the probe 3 illustrated in FIG. 2, and the static gradient magnetic field is applied by using the coil 8 or the like (S21 in FIG. 10).

Next, the interval 2τ of the multiplexed π pulse to be applied to the sample, namely a frequency of the dynamic noise f to be measured is determined (S22 in FIG. 10).

Next, the measurement position corresponding to a gradient of the applied magnetic field is determined (S23 in FIG. 10). Specifically, a frequency and a phase of an RF magnetic field are determined.

Next, using the application portion 5, the magnetic pulse is introduced into the probe 3, and the multiplexed π pulse is applied to the sample at the interval 2τ determined in Step S22 (S24 in FIG. 10).

Next, the generalized transverse relaxation time $T_2^L$ is determined from the NMR signal (S25 in FIG. 10).

Thus, the generalized transverse relaxation time $T_2^L$ at the measurement position determined in Step S23 is determined.

Next, in order to determine the generalized transverse relaxation time $T_2^L$ at a different measurement position, the flow returns to Step S23 (S26 in FIG. 10), and the measurement position is determined again. In accordance with the number of positions to be measured, Steps S23 to S25 are repeated.

When measurement at every position is finished, the generalized transverse relaxation time $T_2^L$ of the sample corresponding to the frequency of the dynamic noise f determined in Step S22 is determined (S27 in FIG. 10).

Next, in order to determine the generalized transverse relaxation time $T_2^L$ at a different frequency of the dynamic noise f, the flow returns to Step S22 (S28 in FIG. 10), and the multiplexed π pulse interval 2τ is determined again. Steps S22 to S27 are repeated in accordance with the number of frequencies to be measured.

When measurement at every frequency is finished, finally, an image of the generalized transverse relaxation time $T_2^L$ of the sample corresponding to various frequencies determined in Step S22 is determined (S29 in FIG. 10).

In this way, the measurement position and the π pulse interval 2τ may be variable.

Thus, the image of the generalized transverse relaxation time $T_2^L$ can be obtained at various measurement positions and π pulse intervals 2τ for the same object to be measured, and hence characteristics of the object to be measured can be understood in more detail.

In this way, according to the second embodiment, the NMR imaging device 1 applies the π pulse to the sample at a predetermined time interval 2τ in a multiplexed manner, so as to perform imaging of the generalized (transverse) relaxation time based on the nuclear magnetic resonance signal of the sample.

Therefore, the same effect as the first embodiment can be obtained.

In addition, according to the second embodiment, the NMR imaging device 1 can obtain the image of the generalized transverse relaxation time $T_2^L$ at various measurement positions and π pulse intervals 2τ.

Therefore, compared to the first embodiment, characteristics of the object to be measured can be understood in more detail.

Example

In the following, this invention is specifically described based on an example.

For each of three types of GaAs, the nuclear magnetic resonance was generated by using the multiplexed π pulse so as to perform imaging of the generalized transverse relaxation time $T_2^L$, and the result was compared to a case where the imaging of the signal attenuation constant $T_2^H$ corresponding to the static transverse relaxation time was performed by using the Hahn echo that was used in a related-art MRI.

First, as samples, three types of materials of substrates were prepared, which include GaAs (undoped), GaAs (Si-doped with a dose of $10^{18}$ cm$^{-3}$), and GaAs (Cr-doped with a dose of $10^{15}$ cm$^{-3}$).

In this example in which the generalized transverse relaxation time $T_2^L$ was determined, an experiment was carried out with such four substrates (each having a thickness of 0.3 mm) that were each cut out to have a size of 10.5 mm by 3.8 mm and stacked.

Further, a capacity of the sample was large so that the experiment in various parameters was able to be carried out in short time in this example, but it is confirmed that the generalized transverse relaxation time $T_2^L$ can be sufficiently determined even if a total amount of target nuclear spins is ¹⁄₄₀ of that at this time.

Therefore, the proposal of this patent application can be applied to a sample of GaAs of at least 1 mm³.

Further, a proton used for the MRI of a living body has a sensitivity of at least 200 times of that of As (because sensitivity is proportional to cube of nuclear gyromagnetic ratio in theory).

Therefore, the generalized transverse relaxation time $T_2^L$ can be determined for a living body sample having dimensions sufficiently smaller than 1 mm³.

Further, the nuclear magnetic resonance device has been manufactured by the applicant et al, which includes an Oxford room temperature bore high resolution NMR superconducting magnet (Oxford 300/89 made in UK), an RF signal generator (HP8656B made in USA), a DC pulse programmer (THAM WAY Corp, N210-1026S made in Japan), a programmable attenuator (TAMAGAWA ELECTRONICS, TPA-410 made in Japan), an RF power amplifier (Doty DSI1000B made in USA), an RF preamplifier (Doty 2L Series made in USA), and the like.

Next, the sample was set in the nuclear magnetic resonance device illustrated in FIG. 2 so as to introduce the multiplexed π pulse to the sample in the static magnetic field, and the generalized transverse relaxation time $T_2^L$ of $^{75}$As was determined from the NMR signal.

Figure 5:
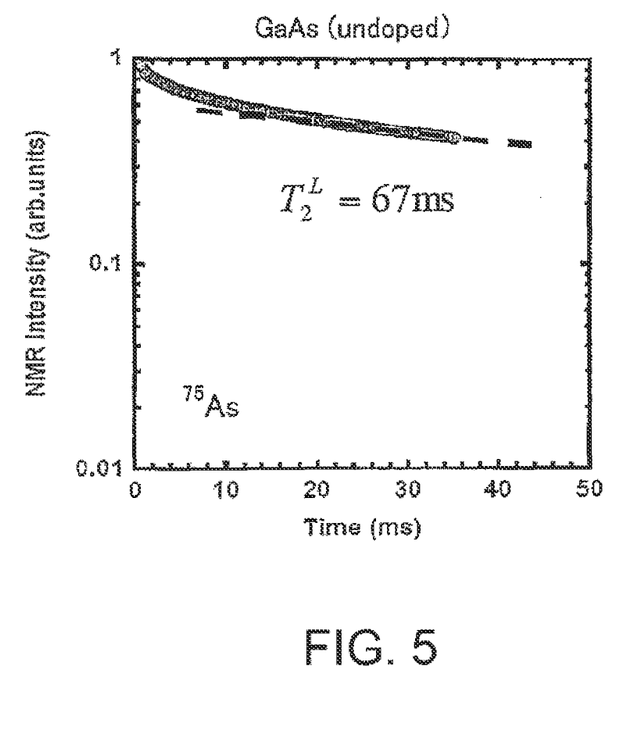
FIG. 5 is a graph showing a relationship between the NMR signal and time when the multiplexed π pulse shown in FIG. 1 is applied to undoped GaAs in the example.
Figure 6:
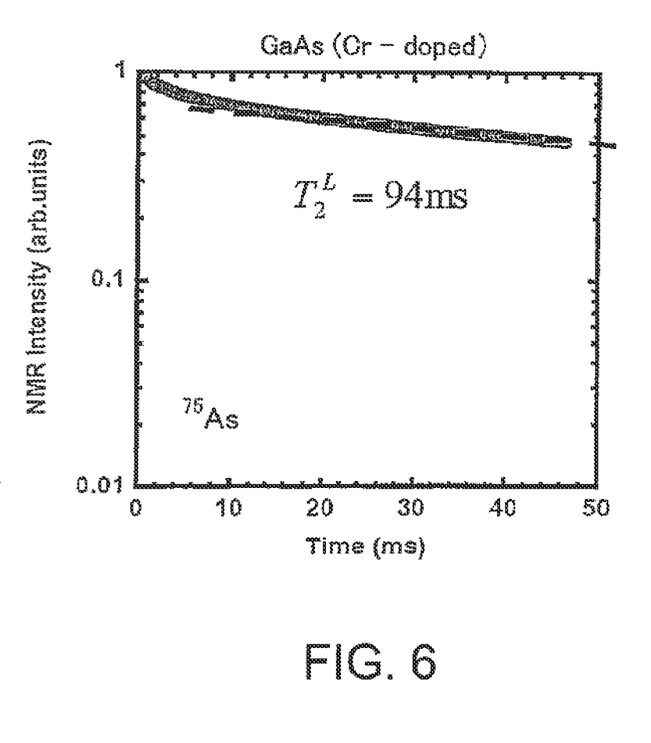
FIG. 6 is a graph showing a relationship between the NMR signal and time when the multiplexed π pulse shown in FIG. 1 is applied to Cr-doped GaAs in the example.

Specifically, first, the multiplexed π pulse was introduced to the sample, and temporal change of intensity of the NMR signal output from the sample was plotted on a logarithm graph as shown in FIGS. 4 to 6.

Next, from the plotted data, an area in which an initial large attenuation was eliminated so that the logarithm of the intensity of the NMR signal was attenuated in proportion to time was determined and fitted by a straight line as shown by a broken line of FIGS. 4 to 6, and hence the signal attenuation constant $T_2^L$ was determined from a gradient of the straight line.

Here, not from the first 180° pulse but a time domain is used in which the intensity of the NMR signal is sufficiently attenuated and the signal intensity is fitted by $M(t) \sim \exp(-t/T_2^L)$.

Further, the π pulse interval 2τ was set to be 100 μs as an interval corresponding to the frequency range in which the interaction between the carriers and the nuclear spins significantly affects noise.

In addition, although the gradient of the static magnetic field is used for obtaining an image in a usual MRI, this experiment was carried out under a constant static magnetic field. This condition is as follows: static magnetic field is 6.16578 T, measuring temperature is 300K, repetition time is 3.0 seconds, and the number of accumulation times is 512 (APCP pulse).

However, because ununiformity of the static magnetic field does not affect the obtaining of $T_2^L$, $T_2^L$ obtained in the example is the same as that in the actual MRI.

Further, as a comparative example, nuclear magnetic resonance was generated in the above-mentioned three types of samples by using the Hahn echo, and the signal attenuation constant $T_2^H$ was obtained. The measurement condition was entirely the same as that of the multiplexed pulse measurement except that the number of accumulation times was 64 and that the signal intensity of the spin echo was measured as a function of τ for first two pulses of the pulse application in FIG. 1 (general Hahn echo measurement).

Figure 7:
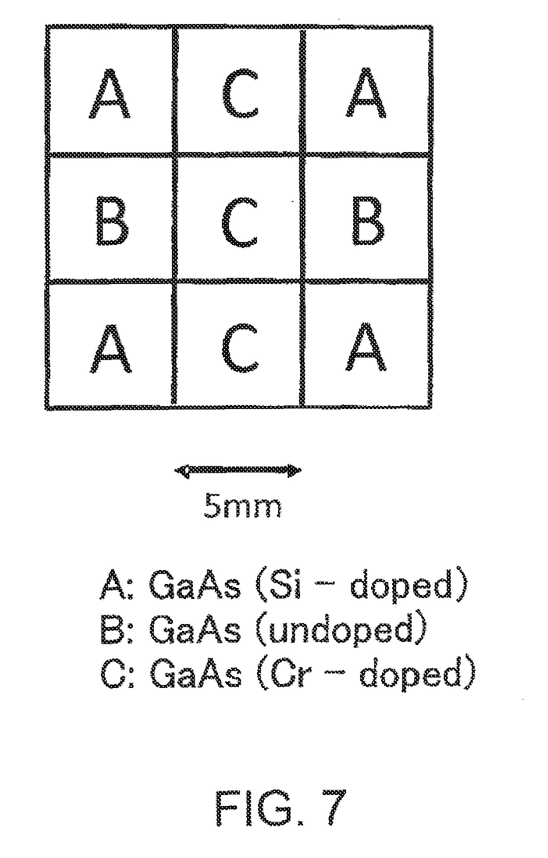
FIG. 7 is a diagram illustrating a layout shape and dimensions of the sample on a plane in the example and a comparative example.

Next, based on the obtained $T_2^L$ and $T_2^H$, the sample was set to have a flat square shape of dimensions of 5 mm by 5 mm (having a thickness of 1 mm), and simulation of imaging was performed for the samples arranged in 3×3 in the layout illustrated in FIG. 7.

Results of calculation of $T_2^L$ and $T_2^H$ are shown in Table 1.

Figure 8:
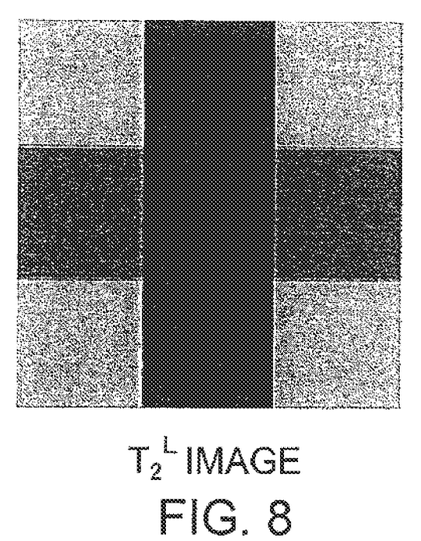
FIG. 8 is a view showing a $T_2^L$ image of FIG. 7 in the example.
Figure 9:
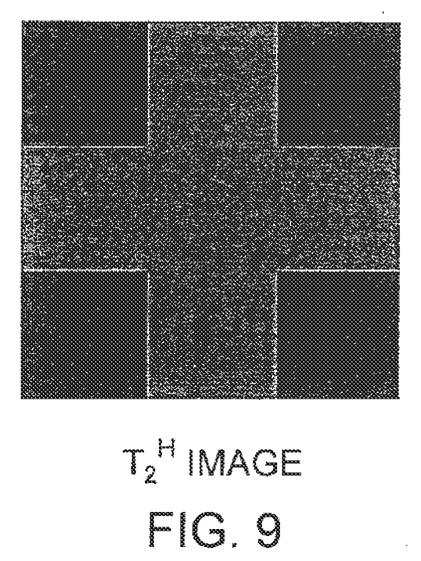
FIG. 9 is a view showing a $T_2^H$ image of FIG. 7 in the comparative example.

In addition, the $T_2^L$ imaged image of this example is shown in FIG. 8, and the $T_2^H$ imaged image of the comparative example is shown in FIG. 9. Further, the imaged image is a gray scale image in which the color density becomes higher as a value of $T_2^H$ or $T_2^L$ is larger (gradation).

TABLE 1

| Sample | GaAs (Si doped) | GaAs (Undoped) | GaAs (Cr doped) |
|---|---|---|---|
| $T_2^H$ | 360 µs | 230 µs | 220 µs |
| $T_2^L(_T = 100 \mu s)$ | 33 µs | 67 µs | 94 µs |

As understood from Table 1 and FIG. 8, a difference of value of $T_2^L$ among samples is obvious (ms order), and the samples were distinguished clearly also in the images.

On the other hand, as shown in Table 1 and FIG. 9, there was a difference of value of $T_2^H$ between GaAs (Si-doped) having a large electron density of $10^{18}$ cm$^{-2}$ and GaAs (undoped) having insulation as well as GaAs (Cr-doped). However, $T_2^H$ of GaAs (undoped) was 220 µs while $T_2^H$ of GaAs (Cr-doped) was 230 µs, and a difference therebetween was very small (10 µs order). Therefore, it was difficult to distinguish between the two samples by $T_2^H$ based on Hahn echo.

From this result, it was found that it was possible to distinguish substances, which was difficult to be distinguished by $T_2^H$, by selecting the appropriate π pulse interval 2τ corresponding to the noise (f) so as to perform the $T_2^L$ imaging.

INDUSTRIAL APPLICABILITY

In this example described above, there is described the case where $^{75}$As imaging of GaAs was performed by using this invention, but this invention is not particularly limited to this example.

For instance, this invention can be applied to $^1$H (proton) or $^{13}$C imaging that is widely used for a living body and in medical MRI.

This is because most of current MRIs detect the NMR signal of water protons in the living body, and protons have higher sensitivity of nuclear to be probed than As that is the object to be measured in this example.

Therefore, it is expected that the noise sensed by protons in the living body (received from the external environment) is also changed significantly depending on a situation in the environment. Thus, by applying this invention to the $^1$H (proton) or $^{13}$C imaging, it can be highly expected in a medical field that lesions that have not hitherto been able to be distinguished can be distinguished similarly to this example in which a difference between GaAs substrates can be distinguished by $^{75}$As.

Further, frequencies of noise that can be detected by the current pulse technology are 100 Hz to a few kHz order, and the frequencies are overlapped with a biological reaction and a response speed of a small part of an organ. Also from this viewpoint, it is expected that it is advantageous to apply this invention to $^1$H (proton) or $^{13}$C imaging.

In addition, it is also expected to apply the solid-state MRI of this example to imaging of many nuclear species other than $^{75}$As.

DESCRIPTION OF SYMBOLS

1 NMR imaging device
3 probe
5 application portion
7 image processing portion

The invention claimed is:

1. An NMR imaging device, comprising:
a probe having a space for housing a sample;
a magnetic field generating portion configured to generate a static magnetic field and a gradient magnetic field in the space of the probe;
a pulse application portion configured to apply a π pulse in a multiplexed manner at a time interval 2τ to the sample placed in the space in which the static magnetic field and the gradient magnetic field are generated as a generated magnetic field; and
an image processing portion configured to receive a nuclear magnetic resonance (NMR) signal output from the sample that is continuously applied with multiple pulses as multiplexed π pulses, fit with a straight line an attenuation curve of intensity of the NMR signal that is obtained after a lapse of a predetermined period of time from the application of the multiplexed π pulses to obtain a gradient of the straight line, determine a transverse relaxation time ($T_2^L$) based on the gradient of the straight line, and perform imaging of the transverse relaxation time,
the NMR signal and the transverse relaxation time ($T_2^L$) having a relationship shown in the following expression (1), $$W(t) \sim \exp(-t/T_2^L) \quad (1)$$

W(t): NMR signal intensity
$T_2^L$: signal attenuation constant (transverse relaxation time)
t: time
the time interval 2τ of the π pulse and a frequency f of noise received by a nuclear spin in the sample from an external environment being expressed by the following expression (2), $$f = \frac{1}{4\tau} \quad (2)$$

f: frequency of noise received by nuclear spin
τ: a half of π pulse interval.

2. The NMR imaging device according to claim 1, wherein the pulse application portion applies the π pulse having the time interval 2τ determined in accordance with a situation of the sample by utilizing a fact that the transverse relaxation time of the NMR signal depends on the time interval 2τ of the π pulse and further that the transverse relaxation time depending on the time interval 2τ of the π pulse depends on the noise received by the nuclear spin from the external environment.

3. The NMR imaging device according to claim 2, wherein the image processing portion performs imaging of the transverse relaxation time by displaying a length of the transverse relaxation time by color gradation.

4. The NMR imaging device according to claim 1, wherein, in a case where the sample is a semiconductor, the pulse application portion selects, as the time interval 2τ of the π pulse, a time interval corresponding to a frequency range in which an interaction between a carrier of the semiconductor and the nuclear spin causes noise.

5. The NMR imaging device according to claim 1, wherein, in a case where the sample is a living body, the pulse application portion selects, as the time interval $2\tau$ of the $\pi$ pulse, a time interval corresponding to a frequency range corresponding to a biological reaction or a response speed of a specific part of an organ.

6. The NMR imaging device according to claim 1,
wherein the pulse application portion is capable of applying the $\pi$ pulse having a Larmor frequency corresponding to the generated magnetic field at a plurality of different positions of the sample to the sample in a multiplexed manner at the time interval $2\tau$, and
wherein the image processing portion is capable of determining the transverse relaxation time $(T_2^L)$ based on the attenuation curve of intensity of the NMR signal that is obtained after a lapse of a predetermined period of time from the application of the multiplexed $\pi$ pulses, for each of the plurality of different positions of the sample so as to perform imaging of the transverse relaxation time.

7. The NMR imaging device according to claim 1,
wherein the pulse application portion is capable of applying a plurality of $\pi$ pulses having different time intervals, and
wherein the image processing portion is capable of determining the transverse relaxation time $(T_2^L)$ based on the attenuation curve of intensity of the NMR signal that is obtained after a lapse of a predetermined period of time from the application of the multiplexed $\pi$ pulses, for each of the plurality of $\pi$ pulses having different time intervals so as to perform imaging of the transverse relaxation time.

8. An NMR imaging method, comprising the steps of:
(a) placing a sample in a probe in which a static magnetic field and a gradient magnetic field are generated as a generated magnetic field;
(b) applying a $\pi$ pulse in a multiplexed manner at a time interval $2\tau$ to the sample placed in the probe in which the static magnetic field and the gradient magnetic field are generated; and
(c) receiving a nuclear magnetic resonance (NMR) signal output from the sample that is continuously applied with multiple pulses as multiplexed $\pi$ pulses, fitting with a straight line an attenuation curve of intensity of the NMR signal that is obtained after a lapse of a predetermined period of time from the application of the multiplexed $\pi$ pulses to obtain a gradient of the straight line, determining a transverse relaxation time $(T_2^L)$ based on the gradient of the straight line, and performing imaging of the transverse relaxation time,
the NMR signal and the transverse relaxation time $(T_2^L)$ having a relationship shown in the following expression (1), $$W(t) \sim \exp(-t/T_2^L) \tag{1}$$

W(t): NMR signal intensity $T_2^L$: signal attenuation constant (transverse relaxation time)
t: time
the time interval $2\tau$ of the $\pi$ pulse and a frequency f of noise received by a nuclear spin in the sample from an external environment being expressed by the following expression (2), $$f = \frac{1}{4\tau} \tag{2}$$

f: frequency of noise received by nuclear spin
$\tau$: a half of $\pi$ pulse interval.

9. The NMR imaging method according to claim 8, wherein the step (b) comprises applying the $\pi$ pulse having the time interval $2\tau$ determined in accordance with a situation of the sample by utilizing a fact that the transverse relaxation time of the NMR signal depends on the time interval $2\tau$ of the $\pi$ pulse and further that the transverse relaxation time depending on the time interval $2\tau$ of the $\pi$ pulse depends on the noise received by the nuclear spin from the external environment.

10. The NMR imaging method according to claim 9, wherein the step (c) comprises performing imaging of the transverse relaxation time by displaying a length of the transverse relaxation time by color gradation.

11. The NMR imaging method according to claim 8, wherein, in a case where the sample is a semiconductor, the step (b) comprises using, as the time interval $2\tau$ of the $\pi$ pulse, a time interval corresponding to a frequency range in which an interaction between a carrier of the semiconductor and the nuclear spin causes noise.

12. The NMR imaging method according to claim 8, wherein, in a case where the sample is a living body, the step (b) comprises using, as the time interval $2\tau$ of the $\pi$ pulse, a time interval corresponding to a frequency range corresponding to a biological reaction or a response speed of a specific part of an organ.

13. The NMR imaging method according to claim 8, wherein the step (b) and the step (c) are repeated while changing the predetermined position of the sample, thereby determining the transverse relaxation time $(T_2^L)$ based on the attenuation curve of intensity of the NMR signal that is obtained after a lapse of a predetermined period of time from the application of the multiplexed $\pi$ pulses, for each of a plurality of different positions of the sample, and performing imaging of the transverse relaxation time.

14. The NMR imaging method according to claim 8, wherein the step (b) and the step (c) are repeated while changing the time interval $2\tau$ of the $\pi$ pulse to be applied to the sample, thereby determining the transverse relaxation time $(T_2^L)$ based on the attenuation curve of intensity of the NMR signal that is obtained after a lapse of a predetermined period of time from the application of the multiplexed $\pi$ pulse, for each of the plurality of $\pi$ pulses having different time intervals so as to perform imaging of the transverse relaxation time.

* * * * *